United States Patent
Kim et al.

(10) Patent No.: US 11,442,034 B2
(45) Date of Patent: Sep. 13, 2022

(54) DUAL HEATER GAS SENSOR MODULE

(71) Applicant: LG ELECTRONICS INC., Seoul (KR)

(72) Inventors: Moosub Kim, Seoul (KR); Insung Hwang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 296 days.

(21) Appl. No.: 16/485,768

(22) PCT Filed: May 31, 2017

(86) PCT No.: PCT/KR2017/005665
§ 371 (c)(1),
(2) Date: Aug. 13, 2019

(87) PCT Pub. No.: WO2018/159899
PCT Pub. Date: Sep. 7, 2018

(65) Prior Publication Data
US 2020/0049645 A1 Feb. 13, 2020

(30) Foreign Application Priority Data
Mar. 3, 2017 (KR) .................. 10-2017-0027695

(51) Int. Cl.
*G01N 27/12* (2006.01)
*G01N 1/24* (2006.01)

(52) U.S. Cl.
CPC ............. *G01N 27/123* (2013.01); *G01N 1/24* (2013.01)

(58) Field of Classification Search
CPC ...... G01N 1/24; G01N 27/123; G01N 27/128; G01N 33/0032; G01N 33/004;
(Continued)

(56) References Cited

U.S. PATENT DOCUMENTS 7,755,466 B2  7/2010  Beck et al.
9,194,834 B2  11/2015 Gaudon et al.
(Continued)

FOREIGN PATENT DOCUMENTS

CN  101427110  5/2009
CN  101458230  6/2009
(Continued)

OTHER PUBLICATIONS

European Patent Office Application Serial No. 17898362.3, Search Report dated Dec. 17, 2020, 9 pages.
(Continued)

*Primary Examiner* — Nimeshkumar D Patel
*Assistant Examiner* — Gedeon M Kidanu
(74) *Attorney, Agent, or Firm* — Lee, Hong, Degerman, Kang & Waimey PC

(57) ABSTRACT

A dual heater gas sensor module according to an embodiment of the present invention comprises: a housing having a front side and a back side which are partially open and forming the exterior of the dual heater gas sensor module; a first gas sensor for heating the air flowing in through the front side of the housing; and a second gas sensor for measuring a specific gas contained in the air discharging through the backside of the housing, wherein the first gas sensor is located in a first region, the second gas sensor is located in a second region that is higher than the first region, and the first region and the second region may be connected by an inclined plane.

7 Claims, 7 Drawing Sheets

(58) Field of Classification Search
CPC .......... G01N 33/0044; G01N 1/2273; G01N 27/125; G01N 27/403; G01N 27/4045; G01N 33/0006; G01N 15/06; G01N 2015/0007; G01N 2015/0046; G01N 2015/0693; G01N 27/122; G01N 27/127; G01N 33/0009; G01N 33/0031; G01N 33/0036; G01N 5/02; B82Y 15/00; H04N 5/2256

See application file for complete search history.

(56) References Cited

U.S. PATENT DOCUMENTS

| | | | |
|---|---|---|---|
| 10,642,322 B2 | 5/2020 | Wang et al. | |
| 2014/0174154 A1* | 6/2014 | Marra | G01N 27/403 73/31.01 |
| 2015/0075253 A1* | 3/2015 | Boyd | G01N 27/4077 73/23.31 |
| 2016/0061761 A1* | 3/2016 | Shim | G01N 27/122 436/151 |
| 2016/0334320 A1* | 11/2016 | Cho | G01N 15/06 |
| 2017/0020032 A1* | 1/2017 | Wang | G06F 1/203 |
| 2020/0049645 A1* | 2/2020 | Kim | G01N 27/128 |

FOREIGN PATENT DOCUMENTS

| | | |
|---|---|---|
| CN | 101750438 | 6/2010 |
| CN | 103718031 | 4/2014 |
| CN | 105424885 | 3/2016 |
| CN | 106153512 | 11/2016 |
| CN | 106358420 | 1/2017 |
| JP | 2014518398 | 7/2014 |
| KR | 20070087946 | 8/2007 |
| KR | 100844966 | 7/2008 |
| KR | 20130084376 | 7/2013 |
| KR | 1020140074269 | 6/2014 |
| KR | 1020160107650 | 9/2016 |
| KR | 1020160134023 | 11/2016 |

OTHER PUBLICATIONS

PCT International Application No. PCT/KR2017/005665, International Search Report dated Nov. 30, 2017, 3 pages.
The State Intellectual Property Office of the People's Republic of China Application Serial No. 201780087026.6, Office Action dated Jun. 3, 2021, 4 pages.

* cited by examiner (a)

(b)

(a)

(b)

(a)          (b)

DUAL HEATER GAS SENSOR MODULE

CROSS-REFERENCE TO RELATED APPLICATIONS

This application is the National Stage filing under 35 U.S.C. 371 of International Application No. PCT/KR2017/005665, filed on May 31, 2017, which claims the benefit of earlier filing date and right of priority to Korean Application No. 10-2017-0027695, filed on Mar. 3, 2017, the contents of which are all hereby incorporated by reference herein in their entirety.

TECHNICAL FIELD

The present invention relates to a dual heater gas sensor module, and more particularly, a gas sensor module which appropriately responds to a temperature change by using the same gas sensor to reduce power consumption.

BACKGROUND ART

A semiconductor type gas sensor using oxide is advantageous in that it has high sensitivity with respect to a gas, has a quick response speed, and is easy to be manufactured when compared to other types of gas sensors and also is enabled to give selectivity to a specific gas by adding a suitable catalyst.

Such a semiconductor type gas sensor utilizes a property in which electrical conductivity at an oxide surface is changed due to adsorption and desorption when a noxious gas is exposed to the surface of a sensing film of the oxide semiconductor. Here, to detect the noxious gas, a temperature of the sensing material constituting the sensing film has to be uniformly maintained to about 300° C. or more.

Thus, there is a problem that a heater for maintaining the sensing film at a temperature higher than a certain temperature is required, and a large amount of power is consumed accordingly.

To solve this problem, micro sensors using a CMOS or a CMOS-MEMS technology is being applied. Also, since the micro sensors have advantages of miniaturization, light weight, low power consumption, a fast response speed, mass production, a low manufacturing cost, and the like, research and development on the micro sensors are being concentrated.

In addition, studies on the development of nano-sized sensing film using nano technologies has been actively carried out to improve the low power consumption and the sensitivity of the gas sensors. Also, since gas sensing characteristics of the semiconductor type gas sensor is due to a surface reaction, the gas sensor using a nano material has low power consumption and high sensitivity characteristics due to a relatively low operation temperature when compared to a bulk sensing film by a high specific surface area of the nano material.

However, to produce a nano sensing film for the gas sensor, there are problems that a considerable accumulated technology is required, and the manufacturing cost is high.

SnO2 is a representative material that forms the sensing film for the gas sensor. SnO2 is a material that exhibits excellent reaction characteristics for various kinds of gases, but there is a disadvantage in selective power consumption stability using only SnO2. Thus, a variety of catalysts are added to increase in the sensitivity characteristics to specific gases. Representatively, CuO exhibits high sensitivity in specific gases such as CO and H2S.

Since gas sensors are usually installed to detect specific noxious gases, appropriate catalysts have to be used to increase in sensitivity characteristics with respect to specific gases. For this, it is important to increase in specific surface area of the sensing film and lower an operation temperature of the gas sensor to minimize the power consumption.

There are a lot of gases in the environment in which we live. That is, there are various gases from armful gases to harmless gases. The harmful gases are generated by general homes, businesses, gas accidents in construction sites, and gas accidents in industries. If the gases are quickly identified to quickly respond to the gas accidents, damage may be minimized. Thus, to effectively cope with each gas, a gas sensor using physical and chemical properties of the material has been developed and used for accident prevention, concentration measurement, alarm, and the like.

The gas sensors are largely classified into semiconductor type gas sensors, solid electrolyte type gas sensors, electrochemical type gas sensors, contact combustion type gas sensors, crystal power generation type gas sensors, and the like, which are classified into physical properties and phenomena. In the above-described types, a gas that is capable of being measured and sensed is determined by a sensing material.

In general, the semiconductor type gas sensors use a change in electrical conductivity depending on the gas passing through the sensing material on a surface of a ceramic semiconductor. Tin oxide (SnO2) is often used as the sensing material. The significance of the sensing material in the semiconductor type gas sensor is indescribable. However, the importance of a heater for effective and efficient reaction of the sensing material with the gas is the key in development of the gas sensor.

A heater of the semiconductor type gas sensor, which is being developed and being commercialized rapidly is implemented in th form of MEMS to response to mobile phones and IOT. The MEMS type heater is the key in implementing low power consumption and is becoming the basis for miniaturization. The gas that is capable of being measured may vary even with the sensors made of the same sensing material according to the driving of the MEMS type heater. When the sensing material quickly and safely reaches a desired temperature, the gas sensor may accurately and quickly respond. The heater is a main indicator in performance of the gas sensor. For this reason, the driving and utilization of the heater may be an important factor of the gas sensor. It affects the lifespan of the heater according to the driving, and it is also a main factor with respect to long term reliability and lifespan of the sensor.

DISCLOSURE OF THE INVENTION

Technical Problem

One object of the present invention is to provide a gas sensor module that is easy to control a reaction speed, uniform air flow maintenance, and residual gas removal in a gas sensor.

Another object of the present invention is to provide a gas sensor module that is capable of quickly responding to an external temperature change by using heater temperature characteristics.

Technical Solution

A dual heater gas sensor module according to an embodiment of the present invention includes a housing having front and rear surfaces, which are partially opened, the housing being configured to define an outer appearance of the dual heater gas sensor module, a base coupled to the housing to define an accommodation space, wherein the base has a first region and a second region, which are disposed at heights different from each other, wherein the first region and the second region are connected to each other through an inclined surface, a first gas sensor coupled to a top surface of the first region of the base to heat the air introduced through the front surface of the housing, and a second gas sensor coupled to a top surface of the second region of the base to measure a specific gas contained in the air discharged through the rear surface of the housing.

Also, the dual heater gas sensor module may further include a micro pump installed on the front surface of the housing of the dual heater gas sensor module according to an embodiment of the present invention and configured to allow the air introduced through the front surface of the housing to move in a direction of the rear surface of the housing.

Also, the first gas sensor of the dual heater gas sensor module according to an embodiment of the present invention may not be provided with a sensing material.

Also, in the dual heater gas sensor module according to an embodiment of the present invention, the outflow hole of the rear surface of the housing may be disposed at a position higher than that of the inflow hole of the front surface of the housing from the ground.

Also, the dual heater gas sensor module according to an embodiment of the present invention may further include a controller configured to control an operation of the dual heater gas sensor module, wherein the controller may set the second gas sensor through a driving resistance value and a driving voltage value, which are set as offset values when the dual heater gas sensor module operates.

Also, the controller of the dual heater gas sensor module according to an embodiment of the present invention may control the dual heater gas sensor module to sense an external temperature change after a preset time elapses, read a resistance change value of the first gas sensor when the temperature change is sensed, and change the driving resistance value and the driving voltage value of the second gas sensor to correspond to the resistance change value of the first gas sensor.

Also, in the dual heater gas sensor module according to an embodiment of the present invention, the housing and the base may be coupled to each other through a joint part.

Also, a metal part configured to facilitate electrical connection between the first gas sensor and the second gas sensor is mounted on each of top and bottom surfaces of the base of the dual heater gas sensor module according to an embodiment of the present invention.

Advantageous Effects

The present invention has the effects as follows.

According to an embodiment of the various embodiments of the present invention, there is the technical effects in which the micro pump is added to the air inflow part to realize the quick response speed, maintain the air flow, and quickly remove the residual gas.

According to another embodiment of the various embodiments of the present invention, the two gas sensors that are the same may be used so that one is used as the reference sensor, and the other is used as the measurement sensor to improve the accuracy of the reference value and also improve the sensor accuracy.

MODE FOR CARRYING OUT THE INVENTION

Hereinafter, embodiments relating to the present invention will be described in detail with reference to the accompanying drawings. The suffixes "module" and "unit" for components used in the description below are assigned or mixed in consideration of easiness in writing the specification and do not have distinctive meanings or roles by themselves.

Figure 1:
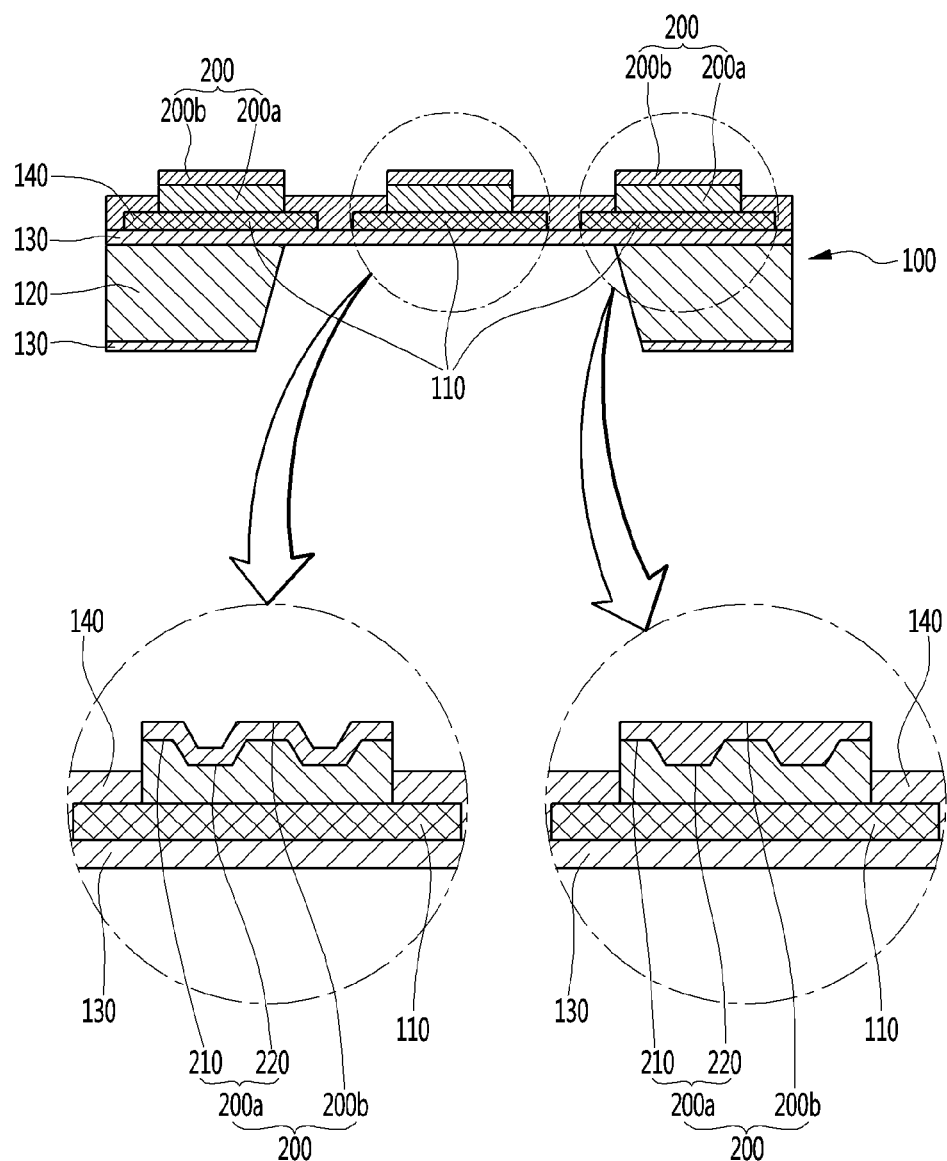
FIG. 1 is a cross-sectional view illustrating an example of a semiconductor type gas sensor.

FIG. 1 is a cross-sectional view illustrating an example of a semiconductor type gas sensor.

A semiconductor type gas sensor according to the present invention is provided with a plurality of heaters and an electrode 110 on a predetermined substrate 100. A first thin film material and a second thin film material are sequentially deposited on an active area of the substrate 100 and then thermally oxidized to form a heterogeneous oxide sensing film 200 constituting a first thin film 200a and a second thin film 200b.

Particularly, in the present invention, the first thin film 200a includes a protrusion part 210 and a groove part 220, which are repeatedly provided. The protrusion part 210 may mean a thick portion, and the groove part may mean a thin portion. Thus, the first thin film 200a disposed on the active area of the substrate 100 may be formed by alternatively repeating the protrusion part 210 and the groove part 220 more than once.

Preferably, the first thin film material may be Sn, and the second thin film material may be Cu. When the first thin film material and the second thin film material are deposited and then thermally oxidized, the heterogeneous oxide sensing film in which the first thin film and the second thin film are combined may be formed. The thin film 200a formed by the thermal oxidization may be $SnO_2$, and the second thin film 200b formed by the thermal oxidization may be $CuO$. The first thin film 200a may mainly constitute the heterogeneous oxide sensing film 200, and the second thin film 200b may serve as a catalyst. That is, the second thin film 200b may be a material that is added to improve sensitivity characteristics of the gas sensor with respect to a specific gas.

The second thin film 200b coupled to the first thin film 200a may have an uneven shape like that of the first thin film or a smooth plan shape.

According to the present invention, since the first thin film is basically constituted by the protrusion part 210 and the groove part 220, the second thin film 200b coupled on the first thin film 200a may have an unevenness having the same shape as the first thin film 200a.

In this case, the second thin film 200b may have a uniform thickness on a whole regardless of its position.

When the second thin film 200b covering the first thin film 200a has the smooth plan shape on a whole, the second thin film 200b disposed on the protrusion part 210 of the first thin film 200a may have a thin thickness, and the second thin film 200b disposed on the groove part 220 of the first thin film 200a may have a thick thickness.

That is, the second thin film 200b may be formed so that the second thin film 200b fills the groove part 220 of the first thin film 200a to provide a uniform height as a whole.

Also, in the semiconductor type gas sensor according to the present invention, the heterogeneous oxide sensing film 200 may have an operation temperature of 200° C.

In the case of the known gas sensor, sensitivity characteristics with respect to a specific gas may be usually maximized at an operation temperature of 300° C. to 400° C. However, in the case of the present invention, the detection sensitivity characteristics with respect to the gas may be maximized at a temperature of 200° C. to reduce power consumption.

Also, according to the present invention, since the first thin film 200a is formed so that the protrusion part 210 and the groove part 220 are alternately repeatedly formed, a specific surface area of the heterogeneous oxide sensing film 200 may be maximized, and also, coupling strength of the second thin film 200b coupled on the first thin film 200a may be improved.

When the first thin film material is deposited on the predetermined substrate 100 that is prepared, and then, the second thin film material is deposited on the first thin film material so that heat is applied to perform thermal oxidation, the heterogeneous oxide sensing film 200 constituted by the first thin film 200a and the second thin film 200b is formed.

In more detail, the first thin film material is deposited on the active area of the substrate 100. Here, the first thin film material may be formed so that the protrusion part 210 having the thick thickness and the groove part 220 having the thin thickness are repeatedly formed.

When the first thin film material is formed, the second thin film material may be deposited on the first thin film material. Thereafter, when the thermal oxidation is formed after 8 hours at a temperature of 800° C., the semiconductor type gas sensor on which the heterogeneous oxide sensing film 200 in which the first thin film 200a and the second thin film 200b are coupled to each other is formed may be manufactured.

Here, the first thin film 200a may be made of $SnO_2$, and the second thin film 200b may be made of CuO.

Also, the first thin film material containing Sn is deposited through thermal evaporation method because Sn has a melting point of 230° C. The second thin film material containing Cu is deposited through E-beam evaporation because the second thin film material has a relatively high melting point (Cu has a melting point of 1080° C.)

Figure 2:
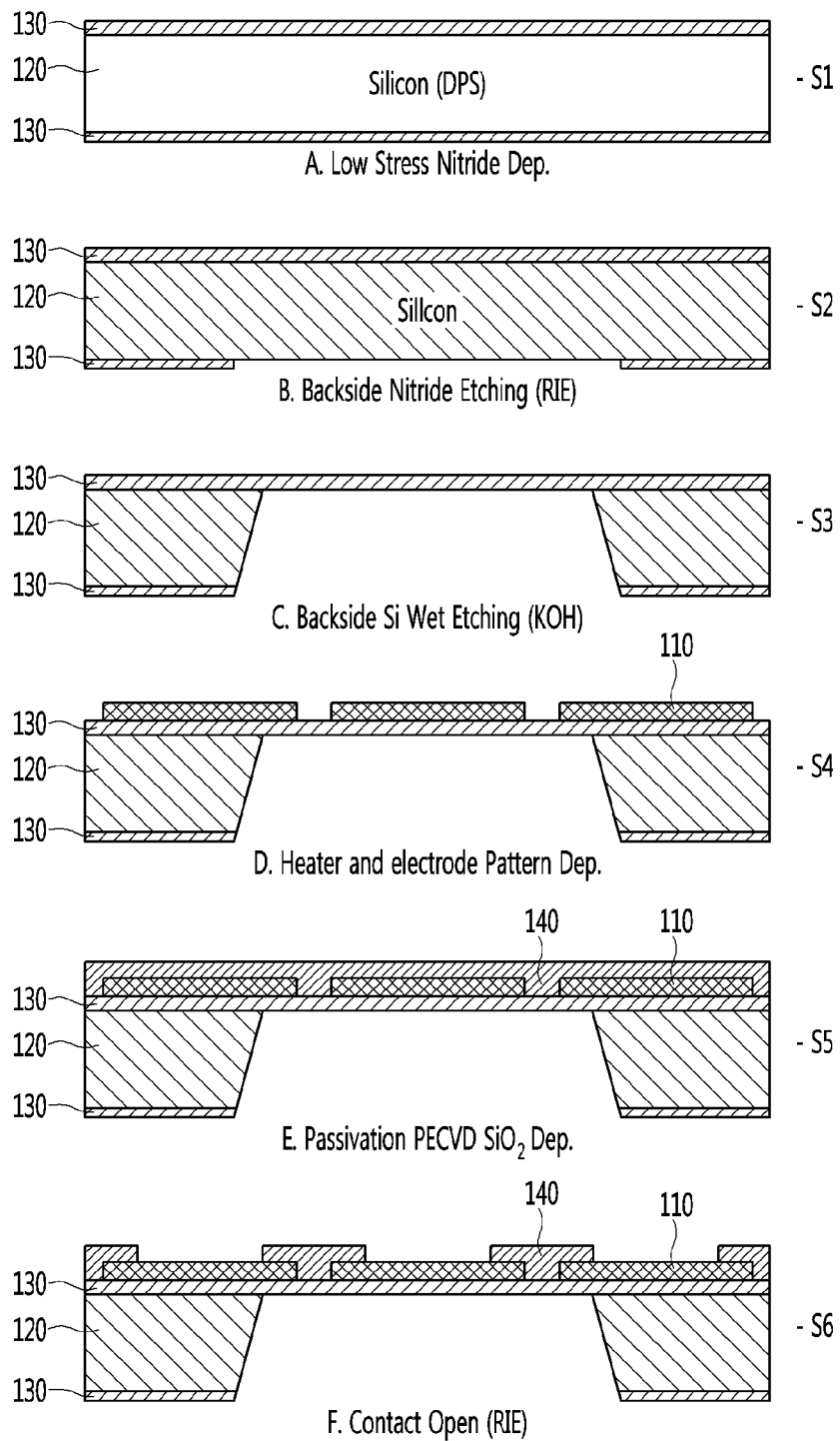
FIG. 2 is a view for explaining a process of manufacturing a semiconductor type gas sensor substrate.

FIG. 2 is a view for explaining a process of manufacturing the semiconductor type gas sensor substrate.

The predetermined substrate 100 to which this embodiment is applied may be based on a silicon substrate. The substrate 100 is manufactured through a nitride film deposition process (S1), a patterning process (S2), an etching process (S3), a lift-off process (S4), a passivation process S5), and an active area formation step (S6).

The nitride film deposition process (S1) is a process of depositing a nitride film 130 on top and bottom surfaces of a prepared silicon plate 120. The patterning process (S2) is a process of removing a portion of the lower nitride film 30 deposited on the silicon plate 120. Here, the nitride film is removed through reactive ion etching (RIE).

The lower nitride film 130 of the silicon plate 120 may be partially removed, and then, a portion of the silicon plate 120 is removed through the etching process (S3).

In the etching process (S3), the etching is performed by using a KOH solution.

Next, the left-off process (S4) of forming a heater and an electrode 110 on the nitride film 130 on the top surface of the silicon plate is performed.

In the left-off process (S4), the heater and the electrode 110 are formed on the nitride film 130 by using a mask.

When the heater and the electrode 10 are formed on the nitride film 130, an $SiO_2$ deposition film 140 is formed to cover the heater and the electrode 110 through the passivation step (S5).

The electrode and the heater 110 may be completely insulated from each other through the passivation step (S5).

Next, the activation area formation process (S6) of removing a portion of the $SiO_2$ deposition film 140 through the RIE to expose the heater and the electrode is performed.

When the substrate 100 having the active area is completely formed through the above-described processes, the heterogeneous oxide sensing film 200 is formed on the active area of the substrate.

Figure 3:
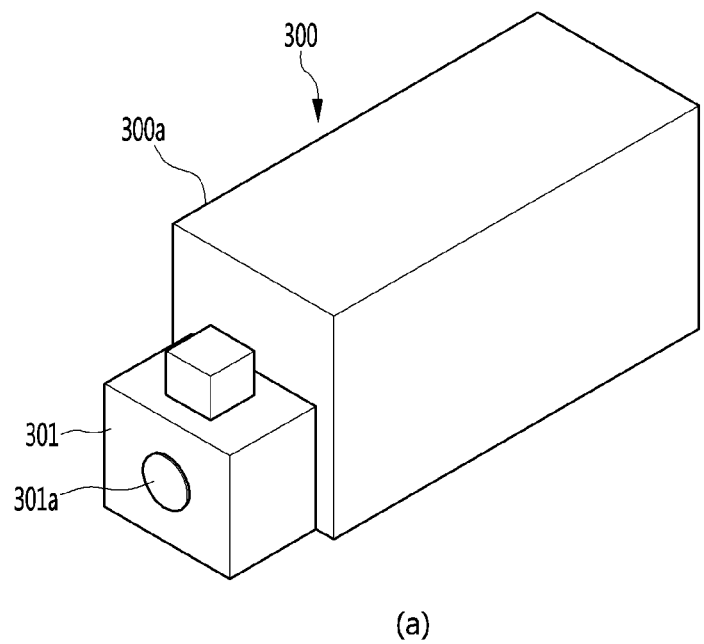
FIGS. 3 and 4 are views for explaining a structure of a dual heater gas sensor module according to an embodiment of the present invention.
Figure 3:
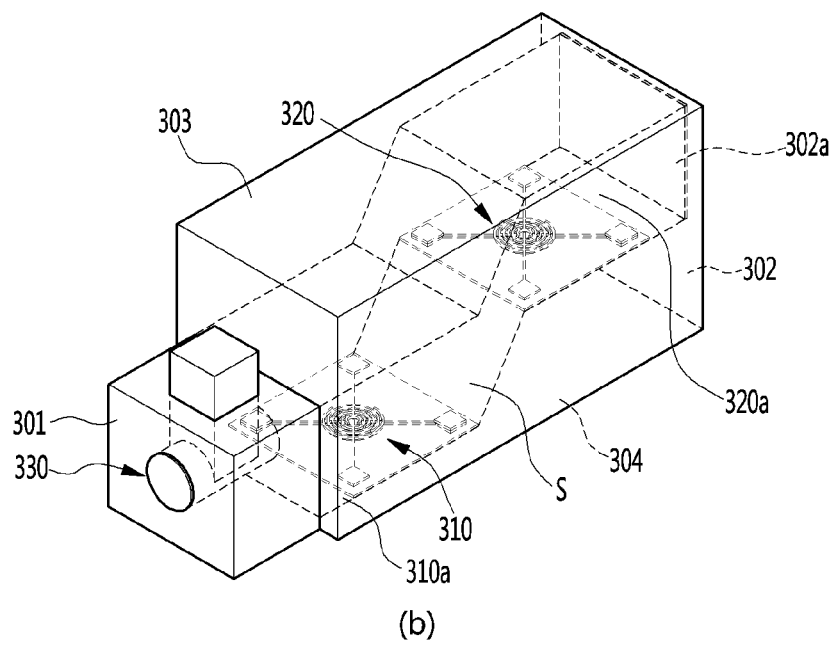
Figure 4:
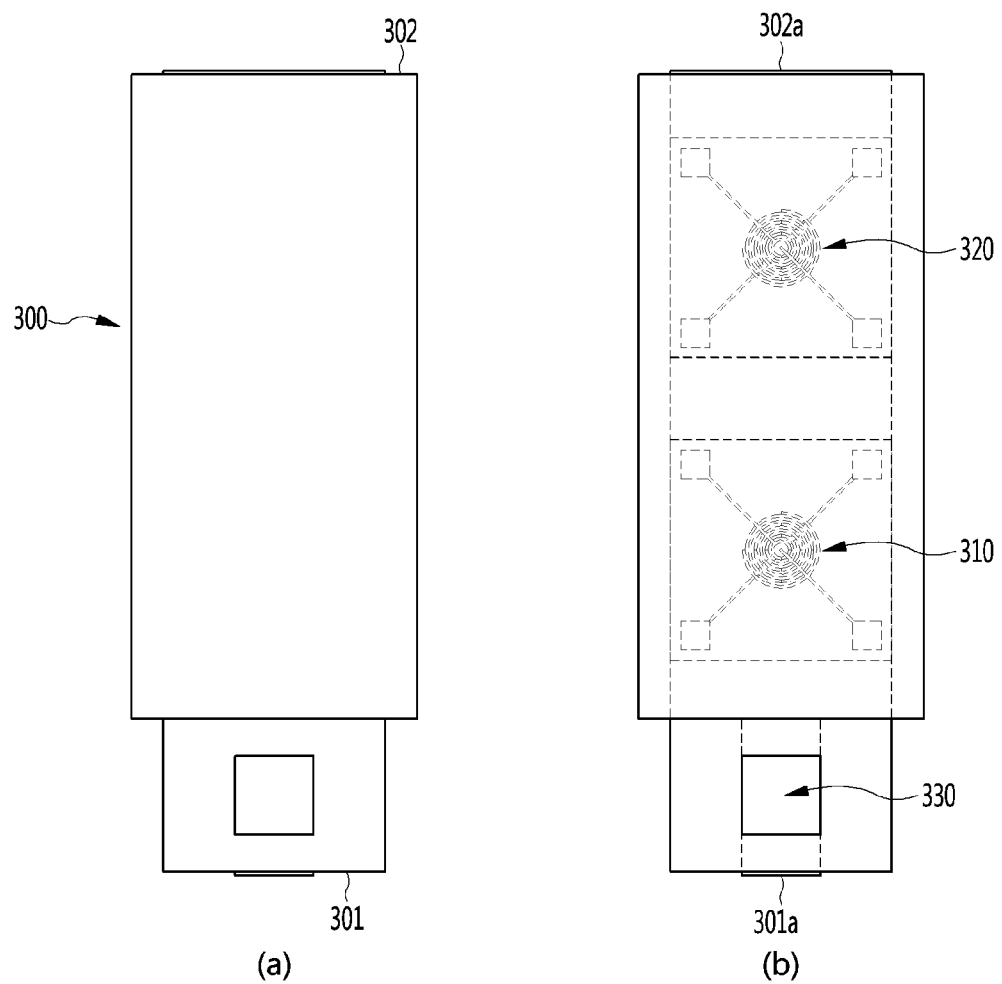

FIGS. 3 and 4 are views for explaining a structure of a dual heater gas sensor module according to an embodiment of the present invention.

As illustrated in FIGS. 3 and 4, a dual heater gas sensor module 300 according to an embodiment of the present invention may include two semiconductor type gas sensors 310 and 320 and a micro pump 330 that adjusts an inflow of air.

Also, the dual heater gas sensor module 300 may include a housing 300a defining an outer appearance of the dual heater gas sensor module 300. The housing 300a may include an inflow hole 301a, through which air is introduced, and an outflow hole 302a through which air is discharged. Here, the inflow hole 301a and the outflow hole 302a are formed by opening portions of a front surface 301 and a rear surface 302, respectively.

The inflow hole 301a formed in the front surface of the housing 300a may have a height less than that of the outflow hole 302a formed in the rear surface 302 of the housing 300a.

The inflow hole 301a formed in the front surface of the housing 300a may have a size less than that of the outflow hole 302a formed in the rear surface 302 of the housing 300a. The inflow hole 301a formed in the front surface 301 of the housing 300a may have a circular shape, and the outflow hole 302a formed in the rear surface of the housing 300a may have a rectangular shape. Thus, the air may be smoothly introduced into the dual heater gas sensor module 300 and be smoothly discharged to the outside through the outflow hole 302a.

As illustrated in FIG. 3, a first gas sensor 310 and a second gas sensor 320 may be disposed at heights different from each other with respect to the ground.

That is, the dual heater gas sensor module 300 may have a stepped structure at a center so that a height difference occurs between the first gas sensor 310 and the second gas sensor 320.

Particularly, the first gas sensor 310 is disposed in a first region 310a, and the second gas sensor 320 may be disposed in a second region 320a. The first region 310a and the second region 320a may have heights different from each other. Particularly, the first region 310a may have a height less than that of the second region 320a. Thus, the first region 310a and the second region 320a may be connected to each other through an inclined surface S.

The first gas sensor 310 may serve as a reference sensor having a shape in which a sensing material is excluded from a measurement sensor as the semiconductor type gas sensor.

The second gas sensor 320 may serve as a measurement sensor in which a heater and a sensing electrode sensing material are mounted to measure a target gas as the semiconductor type gas sensor.

A heater part of the first gas sensor 310 from which the sensing material is excluded may provide a reference value for accurately driving and generate a flow of air due to a temperature difference by rising a temperature of the air so that the gas quickly reacts in a sensor part of the second gas sensor 320.

The heated air may ascend and move through the stepped structure along the heater part of the first gas sensor 310.

Also, the first gas sensor 310 may serve as a reference sensor and be utilized for predicting the state and lifespan of the heater.

A metal part (not shown) configured to easily connect the first gas sensor 310 to the second gas sensor 320 may be mounted on a top surface 303 and a bottom surface 304 of the housing 300a.

The micro pump 330 may provide functions of adjusting a response speed, and maintaining a uniform air flow direction and an air flow, and a refresh function due to quick discharge of the residual gas in the gas sensor.

Figure 5:
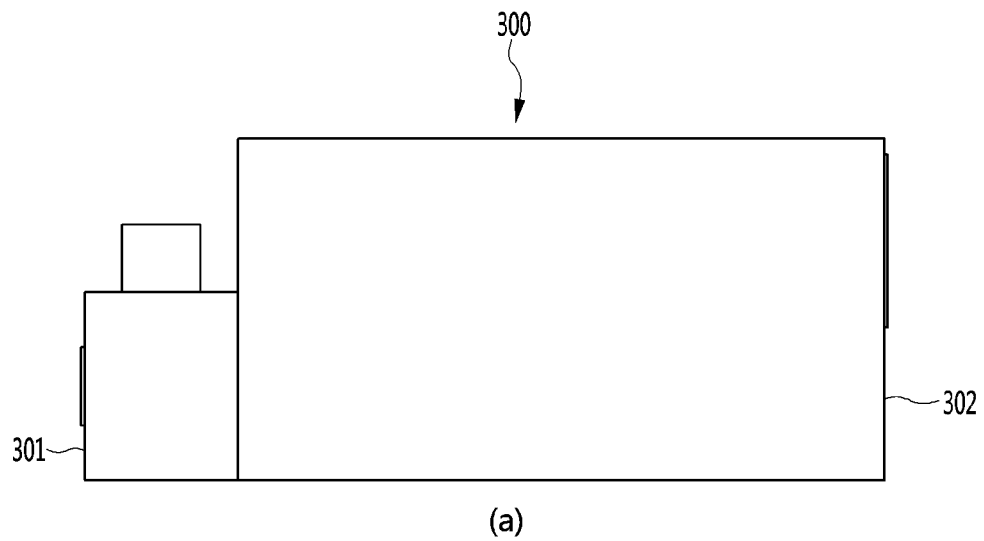
FIG. 5 is a view for explaining the dual heater gas sensor module according to an embodiment of the present invention.
Figure 5:
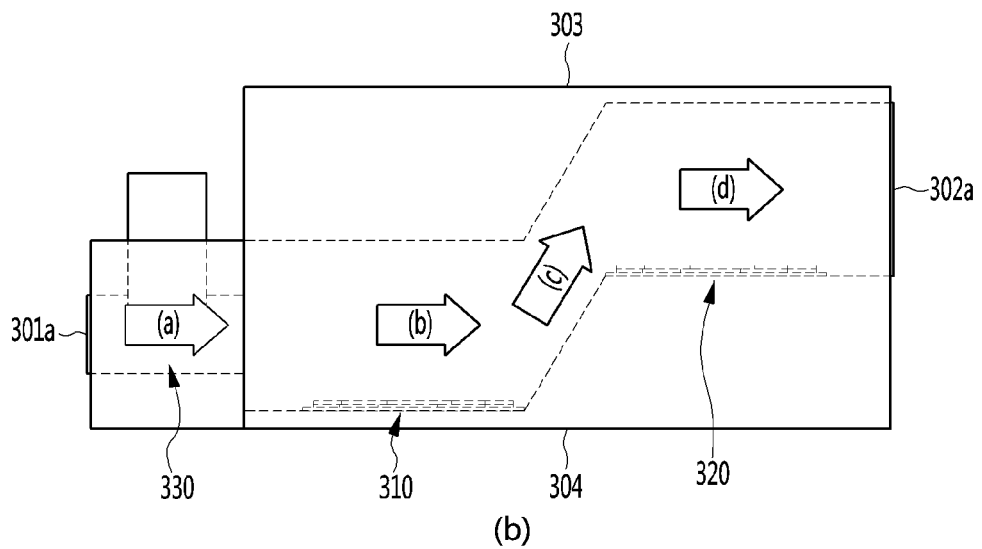

FIG. 5 is a view for explaining the dual heater gas sensor module according to an embodiment of the present invention.

First, air introduced into the micro pump 330 may rise an overall temperature by driving the heater to generate a pressure difference in the first gas sensor 310.

The occurrence in pressure difference due to the passing of the micro pump 330 and the increase of the temperature may derive a quick flow of the heated air and storage of a time taken to react with the sensing material and a quick flow within the system in the sensing part of the second gas sensor 320.

Also, the quick flow may derive absence of the residual gas within the system. This may be an effective technology that is capable of realizing the quick refresh of the gas sensor module.

The air flow path of the gas sensor module may not have a linear shape. This is done because the stepped structure is applied so that the gas heated by a heat source generated in the first gas sensor 310 does not quickly flow to the second gas sensor to prevent the gas from flowing backward.

Thus, the flow of the ascending section-measurement of the heated air introduced into the micro pump 330 may be realized.

The micro pump 330 may be a factor of power increase during low power driving.

Thus, since the generation of the heat source of the first gas sensor 310 generates the flow through the pressure difference, the selective addition may be enabled.

Figure 6:
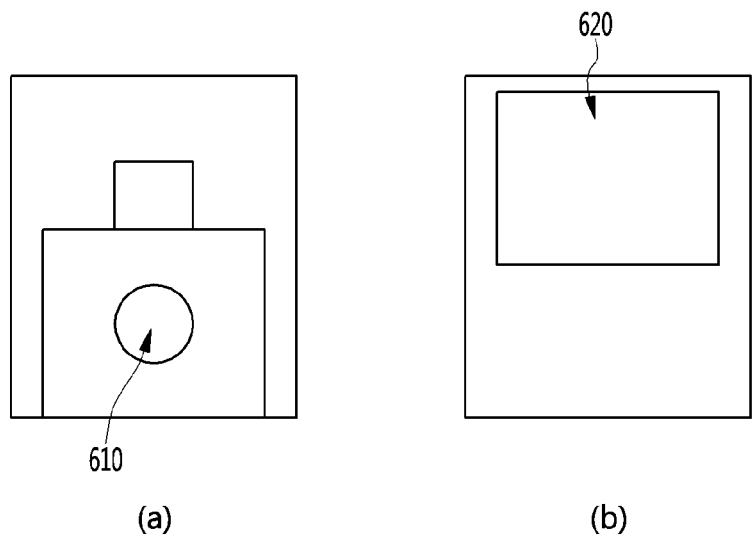
FIG. 6 is a view for explaining an air inflow hole and an air outflow hole of the dual heater gas sensor module according to an embodiment of the present invention.

FIG. 6 is a view for explaining an air inflow hole and an air outflow hole of the dual heater gas sensor module according to an embodiment of the present invention.

As illustrated in FIG. 6, an air inflow hole 610 may be provided in a center of a front surface of the dual heater gas sensor module 300.

A filter may be applied to the air inflow hole 610. The air inflow hole 610 may perform to prevent moisture from being introduced and select a target gas.

Also, an air outflow hole 620 having a rectangular shape may be provided in a rear surface of the dual heater gas sensor module 300.

A filter may be applied to the air outflow hole 620. The air outflow hole 620 may perform functions of smoothly discharging the residual gas within the dual heater gas sensor module and preventing external air from being introduced through the rear surface.

Figure 7:
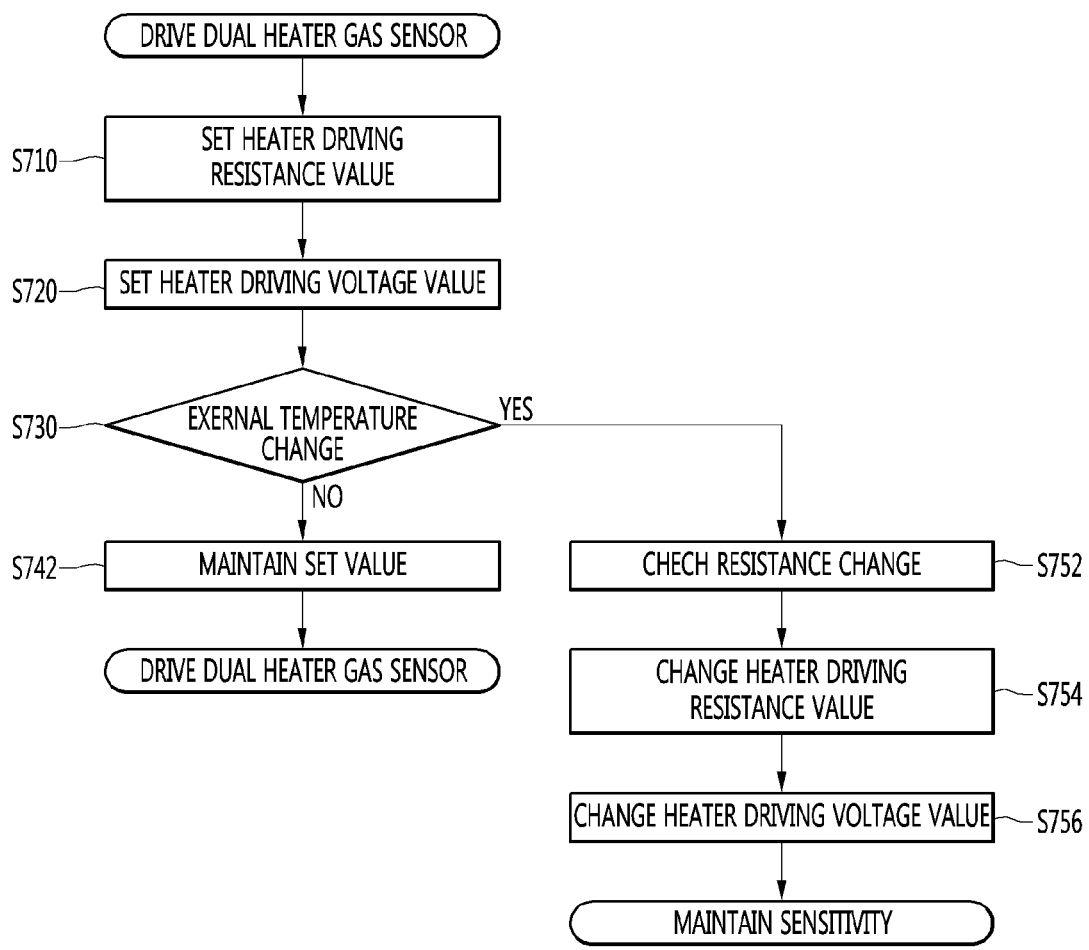
FIG. 7 is a view for explaining a method for driving the dual heater gas sensor module according to an embodiment of the present invention.

FIG. 7 is a view for explaining a method for driving the dual heater gas sensor module according to an embodiment of the present invention.

In case of the gas sensor module according to the related art, even though an external temperature is changed, the change of the external temperature is not reflected.

That is, the gas sensor module is driven at a temperature greater than a driving target temperature due to the influence of the external temperature, and thus, measurement is performed with changed sensitivity instead of accurate sensitivity.

On the other hand, the dual heater gas sensor module according to an embodiment of the present invention may confirm a change of resistance in the first gas sensor 310 to change a resistance value and voltage for correcting the changed resistance value, thereby driving the second gas sensor 320.

Thus, even though an ambient temperature is changed, set sensitivity may be maintained to perform the accurate measurement.

According to the related art, there is a method in which a temperature sensor is installed to be used for the correction. However, this reflects only the change of the external temperature, and thus, influences of the sensing material of the gas sensor and the heater itself are excluded.

Thus, the dual heater gas sensor module according to the present invention may more accurately correct the influence due to the temperature change through the method in which it confirms a change of the reference sensor having the same structure as the measurement sensor.

For example, as illustrated in FIG. 7, when the dual heater gas sensor 300 is driven, driving resistance values of a first gas sensor 310 and a second gas sensor 320 may be set first (S710).

Then, a driving voltage value for measuring a target gas may be set in response to the set driving resistance value (S720).

Also, whether an external temperature changes may be sensed (S730).

When it is determined that the external temperature is not changed as the result of sensing the external temperature change, the set driving resistance value and the set driving voltage value may be maintained (S740).

On the other hand, when it is determined that the external temperature is changed as the result of sensing the external temperature change, a resistance change of the first gas sensor 310 may be checked (S752).

Also, the driving resistance value may be changed according to the resistance change of the first gas sensor 310 (S754), and the driving voltage value may be changed to reduce the power consumption according to the changed driving resistance value (S756).

Thus, in the case of the change of the external temperature, there is a technical effect in which the driving resistance of the second gas sensor 320 is quickly changed through the change of the resistance of the first gas sensor 310 to maximize the reduction of the power consumption.

In the case of the flow path generation method, a physical method for generating a flow path by the stepped portion in the flow path generation method through the heater of the first gas sensor 310 described with reference to FIG. 3 may be exemplified.

This may create an effective flow, but may be accompanied by difficulty in implementation.

A key characteristic of the present invention is that the flow path is generated according to the rising and flowing of the temperature of the measurement gas of the first gas sensor 310.

Thus, even though there is no stepped portion, the derived structure in which the flow path due to the temperature difference is generated may be realized.

In summary, the structure, in which the reference heat source and the generation of the flow path through the reference heat source are provided, and the heat source becomes a core in generation of the flow path and induces the temperature rise of the target gas to lead to the improve the reactivity of the measurement sensor, may be one of the largest technical features of the dual heater gas sensor module.

The above-described dual heater gas sensor module is merely illustrative of the technical idea of the present invention, and various changes and modifications may be made by those skilled in the art without departing from the essential characteristics of the present invention.

What is claimed is:

1. A dual heater gas sensor module comprising:
   a housing comprising a front side in which an inflow hole, through which air is introduced, is defined and a rear side in which an outflow hole, through which air is discharged, is defined, the housing being configured to define an outer appearance of the dual heater gas sensor module;
   a controller configured to control an operation of the dual heater gas sensor module;
   a first gas sensor configured to heat the air introduced through the inflow hole of the front side of the housing, wherein the first gas sensor is not provided with a sensing material; and
   a second gas sensor configured to measure a specific gas contained in the air discharged through the outflow hole of the rear side of the housing,
   wherein air introduced through the inflow hole of the front side flows through a flow path within the housing to be discharged through the outflow hole of the rear side, wherein the flow path is defined by:
   a first region horizontally connected to the inflow hole and comprising a first floor,
   a second region horizontally connected to the outflow hole and comprising a second floor which is higher than the first floor, and
   a third region connecting the first region and second region and comprising an inclined third floor between the first region and the second region,
   wherein the first gas sensor is disposed at the first floor of the first region,
   wherein the second gas sensor is disposed at the second floor of the second region, and wherein the controller is further configured to:
   set a driving resistance value and a driving voltage value of each of the first gas sensor and the second gas sensor as offset values when the dual heater gas sensor module operates,
   sense change of an external temperature,
   read a resistance change value of the first gas sensor when the change of the external temperature is sensed, and
   change the driving resistance value and the driving voltage value of the second gas sensor to correspond to the resistance change value of the first gas sensor.

2. The dual heater gas sensor module according to claim 1, further comprising a micro pump installed on the front side of the housing and configured to allow the air introduced through the front side of the housing to move in a direction of the rear side of the housing.

3. The dual heater gas sensor module according to claim 1, wherein the outflow hole of the rear side of the housing is disposed at a position higher than that of the inflow hole of the front side of the housing.

4. The dual heater gas sensor module according to claim 1, wherein the outflow hole of the rear side of the housing has a size greater than that of the inflow hole of the front side of the housing.

5. The dual heater gas sensor module according to claim 1, wherein the outflow hole of the rear side of the housing has a rectangular shape, and
   the inflow hole of the front side of the housing has a circular shape.

6. The dual heater gas sensor module according to claim 1, wherein the controller is further configured to: control the dual heater gas sensor module to maintain the driving resistance value and the driving voltage value of the second gas sensor when the change of the external temperature is not sensed.

7. The dual heater gas sensor module according to claim 1, wherein a metal part configured to facilitate electrical connection between the first gas sensor and the second gas sensor is mounted on each of top and bottom sides of the housing.

* * * * *